(12) United States Patent
Erickson (10) Patent No.: US 6,578,210 B2
(45) Date of Patent: Jun. 17, 2003

(54) PATIENT ASSISTIVE DEVICE AND LIFT SYSTEM

(76) Inventor: Patricia M. Erickson, 38263 Tottenham, Sterling Heights, MI (US) 48312

( * ) Notice: Subject to any disclaimer, the term of this patent is extended or adjusted under 35 U.S.C. 154(b) by 13 days.

(21) Appl. No.: 09/908,326

(22) Filed: Jul. 18, 2001

(65) Prior Publication Data

US 2002/0148042 A1 Oct. 17, 2002

Related U.S. Application Data

(63) Continuation-in-part of application No. 29/140,219, filed on Apr. 13, 2001.

(51) Int. Cl.$^7$ ................................................. A61G 7/10
(52) U.S. Cl. .............................................. 5/89.1; 5/83.1
(58) Field of Search ........................ 5/89.1, 85.1, 83.1, 5/81.1 R, 81.1 T, 86.1, 87.1; 128/876

(56) References Cited

U.S. PATENT DOCUMENTS

| | | | | | |
|---|---|---|---|---|---|
| 632,826 | A | | 9/1899 | Bunker | 417/332 |
| 1,876,832 | A | * | 9/1932 | Bancroft | 5/89.1 |
| 1,878,785 | A | * | 9/1932 | Leavitt | 5/86.1 |
| 3,137,011 | A | * | 6/1964 | Fischer | 5/86.1 |
| 3,222,029 | A | * | 12/1965 | Hildemann | 5/86.1 X |
| 3,458,878 | A | * | 8/1969 | Combs | 5/81.1 T |
| 3,623,169 | A | * | 11/1971 | James | 5/87.1 |
| 3,694,829 | A | * | 10/1972 | Bakker | 5/87.1 |
| 3,732,584 | A | * | 5/1973 | James | 5/87.1 |
| 3,877,421 | A | * | 4/1975 | Brown | 5/87.1 X |
| 4,117,561 | A | * | 10/1978 | Zamotin | 5/83.1 |
| 4,125,908 | A | | 11/1978 | Vail et al. | 5/83.1 |
| 4,202,064 | A | | 5/1980 | Joergensen | 5/83.1 |
| 4,256,098 | A | | 3/1981 | Swan et al. | 5/85.1 |
| 4,372,452 | A | | 2/1983 | McCord | 212/285 |
| 4,484,366 | A | * | 11/1984 | Koontz | 5/83.1 |
| 4,510,633 | A | * | 4/1985 | Thorne | 5/87.1 |
| 4,571,758 | A | * | 2/1986 | Samuelsson | 5/83.1 |
| 4,682,377 | A | * | 7/1987 | Reich | 5/83.1 |
| 4,700,416 | A | * | 10/1987 | Johansson | 5/81.1 T |
| 4,716,607 | A | * | 1/1988 | Johansson | 5/81.1 T |
| 4,748,701 | A | * | 6/1988 | Marlowe et al. | 5/89.1 |
| 4,793,008 | A | * | 12/1988 | Johansson | 5/81.1 T |
| 4,944,056 | A | | 7/1990 | Schroeder et al. | 5/85.1 |
| 5,123,131 | A | | 6/1992 | Jandrakovic | 5/85.1 |
| 5,158,188 | A | | 10/1992 | Nordberg | 212/312 |
| D362,327 | S | | 9/1995 | Nelson | D34/28 |
| 5,456,655 | A | | 10/1995 | Morris | 601/23 |
| 5,490,293 | A | | 2/1996 | Nilsson | 5/83.1 |
| 5,511,256 | A | | 4/1996 | Capaldi | 5/83.1 |
| D371,333 | S | | 7/1996 | Fennell | D12/128 |
| 5,647,378 | A | * | 7/1997 | Farnum | 5/89.1 X |
| 5,711,044 | A | * | 1/1998 | Newman et al. | 5/81.1 T |
| 5,729,843 | A | * | 3/1998 | Manthey | 5/89.1 |
| 5,815,859 | A | | 10/1998 | Lavin | 5/89.1 |
| 6,073,280 | A | * | 6/2000 | Farnum | 5/89.1 |
| 6,175,973 | B1 | * | 1/2001 | Hakamiun et al. | 5/89.1 |
| D437,263 | S | | 2/2001 | Dahlberg et al. | D12/128 |
| 6,311,346 | B1 | * | 11/2001 | Goldman | 5/81.1 T |
| 2002/0148042 | A1 | * | 10/2002 | Erickson | 5/89.1 |

* cited by examiner

Primary Examiner—Robert G. Santos (57) ABSTRACT

The present invention provides a support assembly for use with a patient lift system, including a support belt and a support strap to support a patient during transport. The support belt includes a longitudinal encasement with a first end and a second end, and an internal compartment. The support belt also includes a central chamber flanked by lateral chambers in the internal compartment and an access opening in the longitudinal encasement with an enclosure mechanism to selectively provide access to the internal compartment. The support strap provided includes a plurality of retainers on the exterior of the support strap. An attachment strap is attached to the support strap through the retainers and the attachment strap has an attachment strap first end and an attachment strap second end. Each of the attachment strap first end and an attachment strap second end have an attachment strap interconnection portion attachable to a rigid structure for securing a patient.

9 Claims, 9 Drawing Sheets

*Figure - 21*

PATIENT ASSISTIVE DEVICE AND LIFT SYSTEM

FIELD OF THE INVENTION

The present invention relates to assistive devices for patients and, more specifically, to assistive devices for suspending non-weight bearing or incapacitated patients via patient lift systems including support devices.

BACKGROUND OF THE INVENTION

Patient lift devices are commonly used with non-weight bearing or incapacitated patients to assist a caregiver in performing a variety of functions. The most common patient lift devices are hydraulic lift systems that are operated by manual or motorized controls to lift and move the patient to a variety of positions. The patient lift devices can be used to transport the patient from a seated or resting position to another resting position, or can be used to transport the patient to a bathing facility, lavatory, or a variety of other locations. The lift device is also useful for helping the caregiver bathe and clothe the patient. The patient lift device must be used in conjunction with some form of a suspension system to support the patient during transport.

Current suspension systems are variations of unitary transfer strap systems that support the entire body of the patient in one continuous saddle or strap assembly. They are connected to the patient lift device at various connection points and thus suspend the patient from the lift device. The conventional suspension systems are uncomfortable and awkward for the patient, as well as difficult or prohibitive for performing certain functions.

The unitary transfer strap suspension system forces the patient's body to conform to an uncomfortable position while being suspended. The surface area in contact with the patient's body can cause pain and discomfort if the patient has fragile skin or lesions, and can exacerbate wounds by tearing the skin. In addition, many current transfer strap systems are painful for an non-weight bearing patient because thin straps do not appropriately distribute or cushion the pressure applied to the patient's body. This can be especially painful for skin, joints, and limbs.

In addition, the nature of the transfer strap current systems make it extremely difficult for a caregiver to assist the patient in certain functions. A transfer strap system of the current design makes it very difficult to dress and undress a patient, as the unitary piece makes it cumbersome to extricate limbs and remove clothing. Also, it is extremely difficult to bathe a patient because of restriction of limb and torso movement in a unitary transfer strap system. Accordingly, the current transfer strap systems increase the risk of a patient falling or being injured, as well as increasing the risk of caregivers injuring themselves while attempting to perform these tasks.

There is a need for a patient lift device suspension system that provides a safe and comfortable suspension system while allowing for increased patient flexibility and mobility while suspended. There is also a need for a system that reduces the pain and physical injuries that a patient, and possibly a caregiver, may sustain while a patient is suspended in the transport lift device.

SUMMARY OF THE INVENTION

Accordingly, the present invention provides a lift system assembly for selective use with a patient assistive lift device, including a support belt and a support strap to support a patient during transport. The configurations available with the lift system assembly provide additional patient limb mobility to facilitate activities, such as dressing, bathing, and assisting with lavatory use.

The lift system assembly support belt includes a longitudinal encasement having a first end, a second end, and an internal compartment. The support belt also includes a structural rib extending from the first end to the second end, and an interconnection portion disposed at both the first end and second end. Each interconnection portion includes a ring for attachment to a patient lift system litate, thus attaching the support belt to the patient lift system.

The lift system assembly support strap includes a primary strap including an encasement with multiple retainers on the exterior of the encasement. An attachment strap is attached to the encasement by being threaded through the retainers. The attachment strap has a first and a second end, with a ring disposed at each end. The ring attaches to the litate of the patient lift system, thus attaching the support strap to the patient lift system.

The lift system devices have components that provide patient comfort with strategic cushioning on the support belt and support strap to reduce pressure on the body. The support belt and support strap design also inhibit chafing and tearing of the skin caused by lateral movement.

The present invention provides a safe and comfortable suspension system for use with a patient lift device for suspending both partial-weight bearing and non-weight bearing patients. Further, the present invention allows for greater mobility of the patient's body while suspended from the patient lift device. Also, the present invention also includes a lower cost material lift system that is flexible, strong, and durable.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following descriptions of the preferred embodiments are merely exemplary in nature and is in no way intended to limit the invention, its application, or uses. Further, certain terminology is used in the following detailed description for convenience only and is not intended to be limiting. For example, the words "front", "back", "upper", "lower", and "above" are intended to designate direction or orientation shown in the drawings to which reference is being made.

A first preferred embodiment of the present invention is depicted in FIGS. 1 through 5. A support belt 10 includes a longitudinal encasement 12 with an internal compartment 14. A structural rib 16 extends the length of the internal compartment 14 of the longitudinal encasement 12 from a first end 18 to a second end 20. The structural rib is attached to a surface 22 of the internal compartment 14 and provides structural integrity to the support belt 10, thereby enabling significant weight bearing capacity. The weight bearing capacity can be enhanced by using a thicker structural rib 16. Although it will be appreciated that numerous materials of construction can be used for construction of the rib, a preferred material is Dacron.

Figure 6:
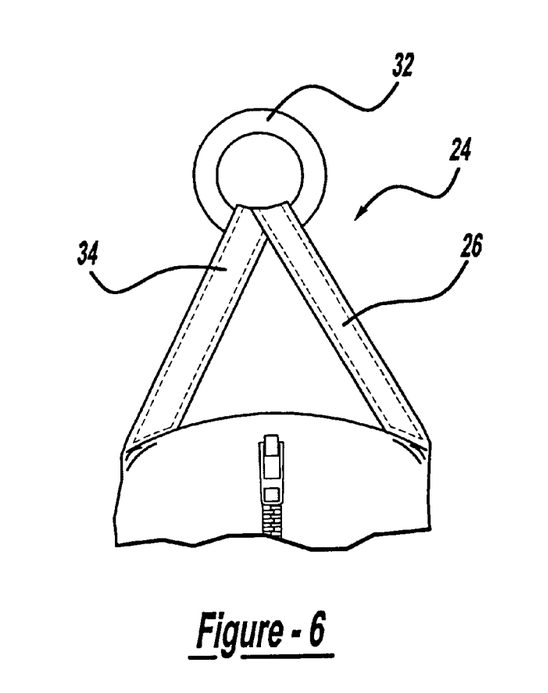
FIG. 6 is a detailed view of an interconnection portion of a support belt including a D ring.
Figure 7:
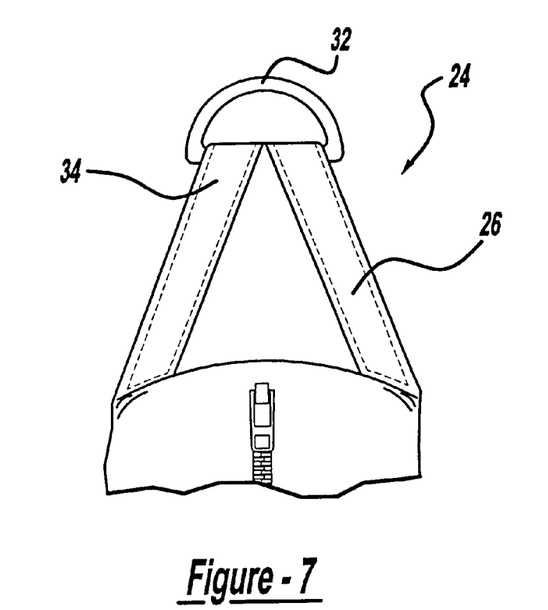
FIG. 7 is a detailed view of an alternate embodiment of an interconnection portion of a support belt including an O ring.
Figure 8:
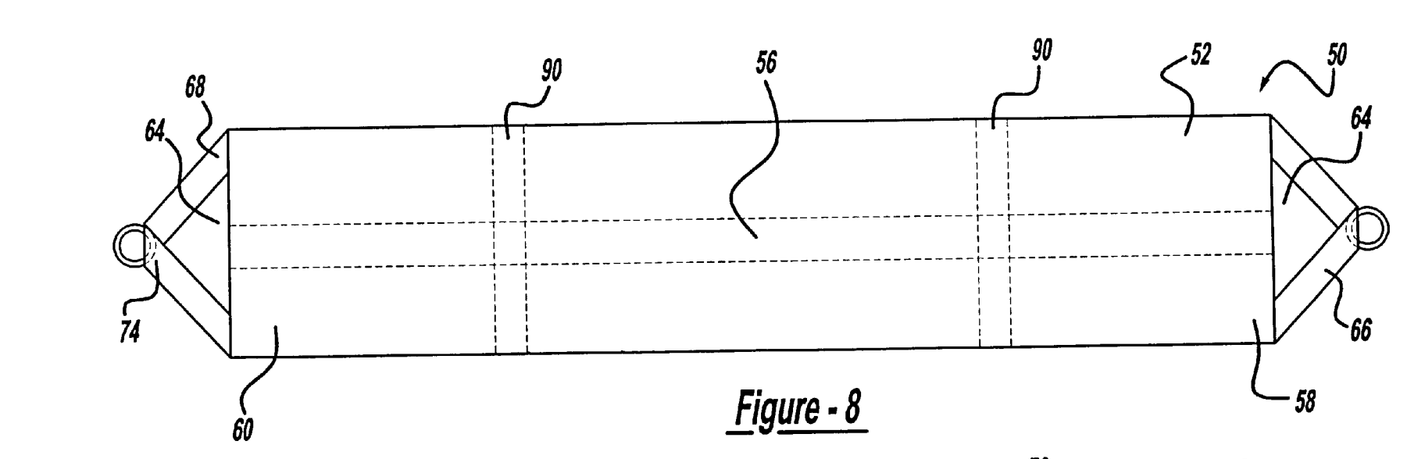
FIG. 8 is a perspective view of a second embodiment of a support belt showing a first side of the support belt.
Figure 9:
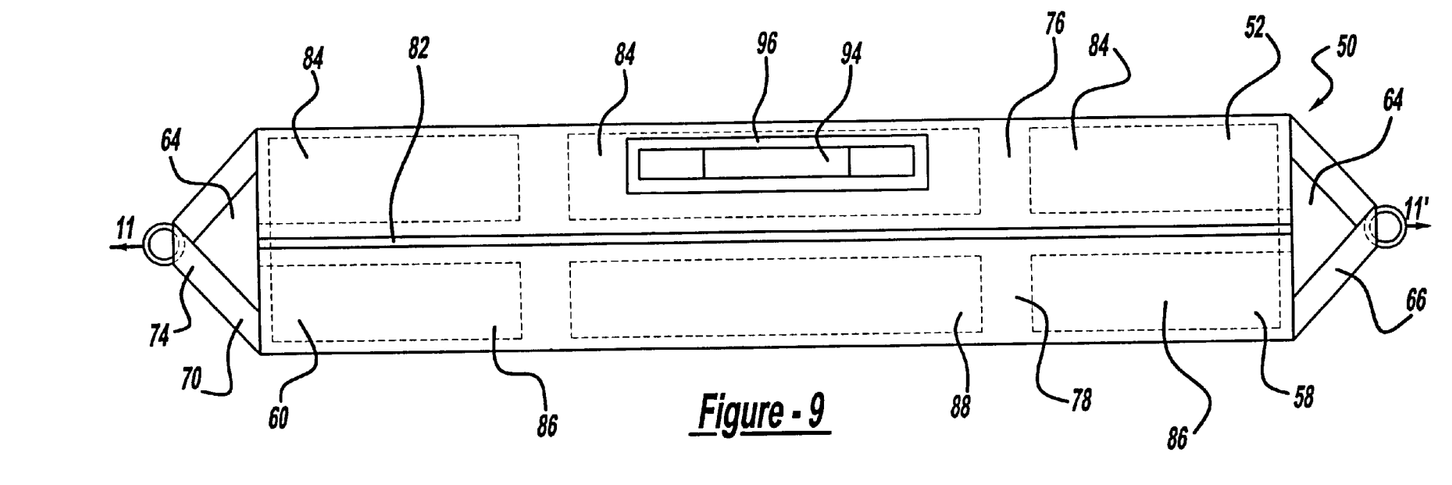
FIG. 9 is a perspective view of a second embodiment of a support belt showing a second and opposing side of the support belt.
Figure 10:
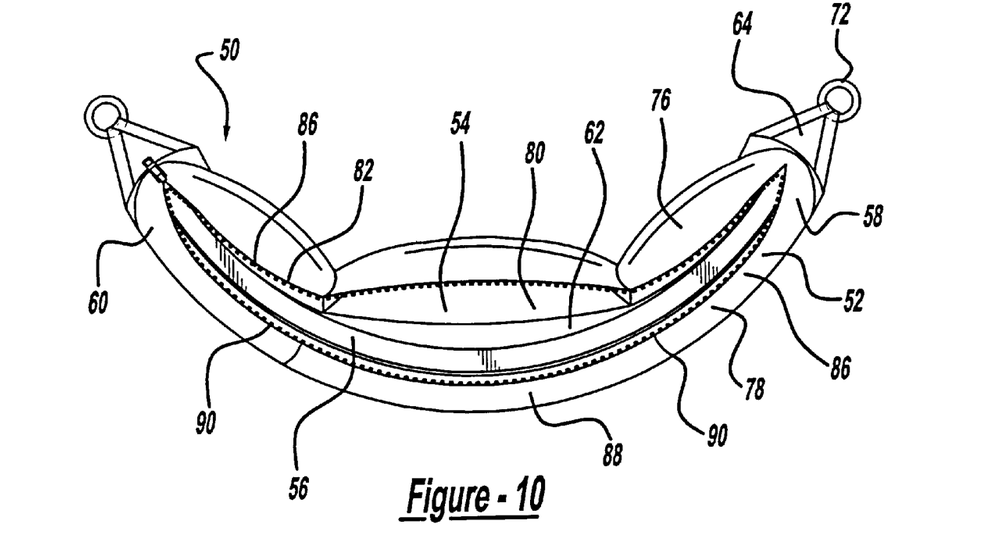
FIG. 10 is a perspective view of the second embodiment of a support belt with an enclosure mechanism opened, exposing an internal compartment.

Both the first and second ends 18, 20 of the longitudinal encasement 12 include interconnection portions 24, that are generally triangularly shaped. Each interconnection portion 24 includes a structural webbing 26 that initiates on a first side 28 of the support belt 10 and folds over to terminate on an opposite, or second side 30, of the support belt 10. The structural webbing 26 generally follows the perimeter of the interconnection portions 24. A ring 32 is attached to the interconnection portion 24 of the support belt 10. The ring 32 is generally affixed to the support belt 10 through a loop enclosure 34 created by the structural webbing 26. The structural webbing 26 is made of a durable and strong material of construction. A preferred material is Dacron. The ring 32 attached to the interconnection portion 24 can be selected as a "D" ring as shown in FIG. 6, or alternatively, an "O" ring, as shown in FIG. 7.

Figure 3:
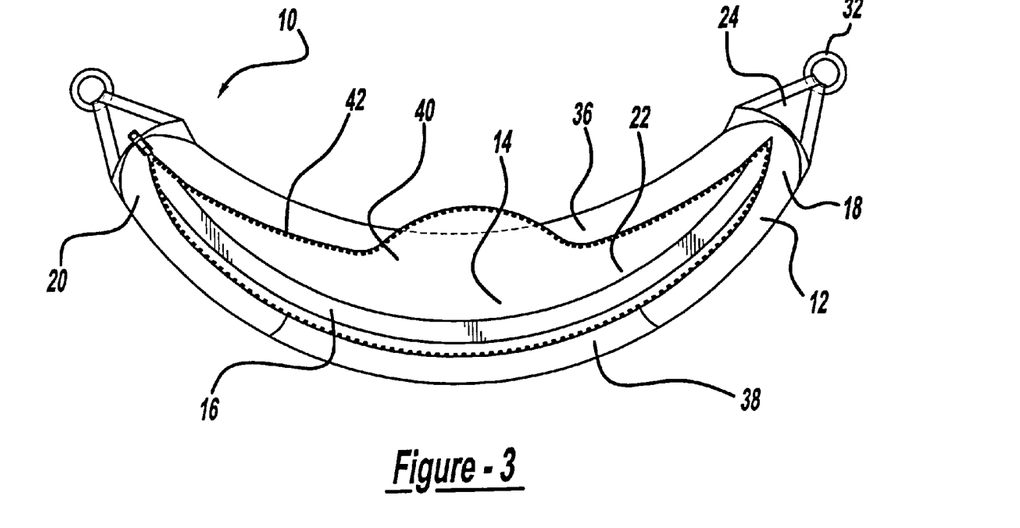
FIG. 3 is a perspective view of the first embodiment of a support belt with an enclosure mechanism opened, exposing an internal compartment.
Figure 4:
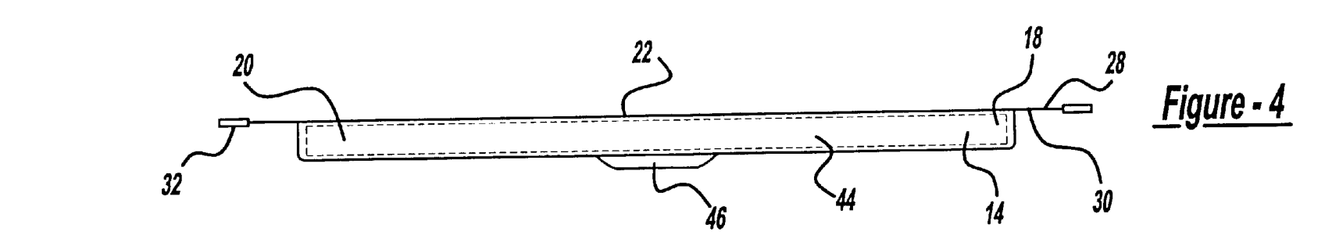
FIG. 4 is a cross sectional view along line 4–4' in FIG. 2 of the first embodiment of a support belt showing an internal compartment with a support pad.
Figure 5:
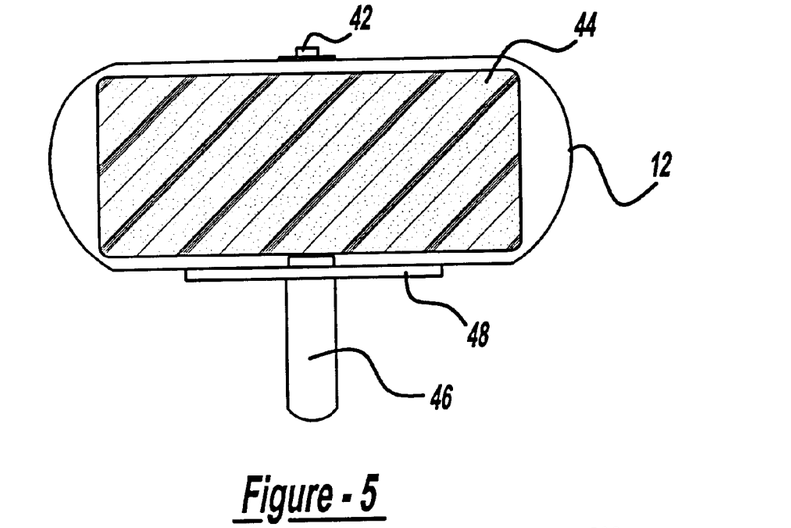
FIG. 5 is cross sectional view along line 5–5' in FIG. 2 of the first embodiment of a support belt.

In the first embodiment of the support belt 10, the first side 28 of the longitudinal encasement 12 contains a first portion 36 and a second portion 38. An access opening 40 formed between the first and second portions 36, 38 enables access to the internal compartment 14. An enclosure mechanism 42 is disposed along each edge of one side of the first and second portions, 36, 38. The enclosure mechanism 42 can be any of those known by one skilled in the art, including a zipper, snaps, hook and loop, or buttons. As shown in FIG. 3, the enclosure mechanism is depicted as a zipper. The zipper 42 holds the first and second portions 36, 38 together, closing the internal compartment 14 of the longitudinal encasement 12.

The internal compartment 14 contains a support padding 44 that can be selectively removed through the access opening 40. The support padding 44 can be enclosed within a launderable case or placed directly into the internal compartment 14. Alternatively, a launderable foam may be used for the support pad eliminating the need for a launderable case. The longitudinal encasement 12 of the support belt 10 may also be constructed of launderable materials. The launderable materials may be necessary if a patient soils the material, or if different patients use the same device, or when sanitation is necessary. The support pad 44 is preferably constructed of foam support padding of a type known to one skilled in the art. A preferred material of construction is an open-cell rebounded urethane-ether foam having a rubber base, having a density of 6–7 lb/ft$^3$, available from such suppliers as the Foam Factory.

Figure 1:
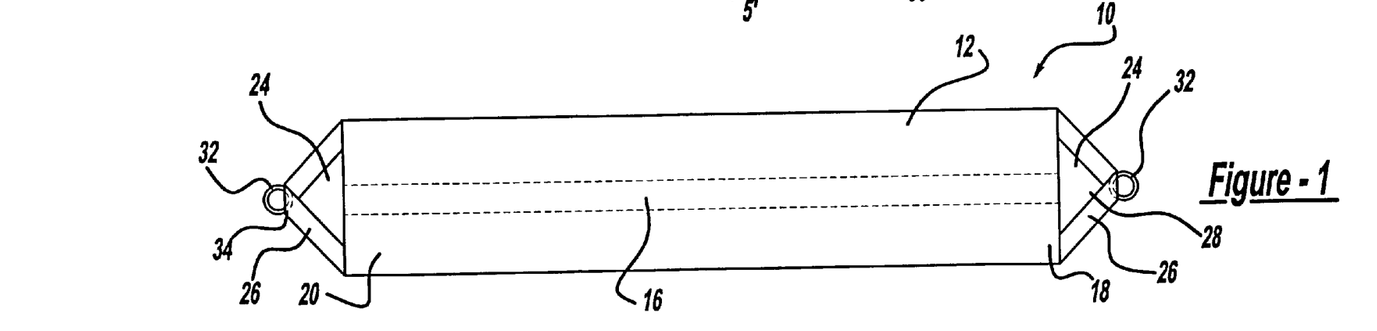
FIG. 1 is a perspective view of the first embodiment of a support belt showing a first side of the support belt.
Figure 2:
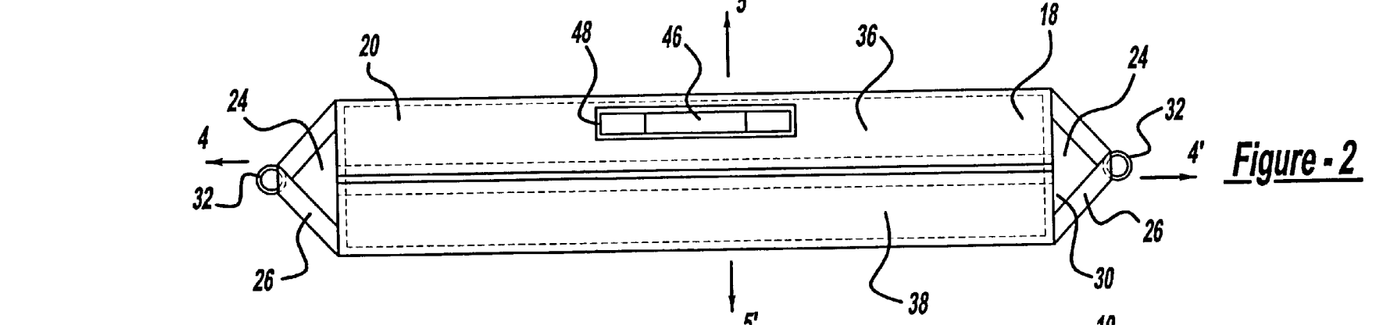
FIG. 2 is a perspective view of the first embodiment of a support belt showing a second and opposing side of the support belt.

The first embodiment also contains a handle 46 disposed on the second side 30 of the support belt 10. The handle 46 is attached to a reinforced area 48 of the second side 30 of the support belt 10. The reinforced area 48 adds structural integrity and endurance to the junction between the longitudinal encasement 12 and the handle 46. The handle 46 may be constructed of any number of durable, strong, flexible materials. The handle is preferably made of Dacron.

A second preferred embodiment of the present invention is shown in FIGS. 8 through 12. A support belt 50 includes a longitudinal encasement 52 with an internal compartment 54. A structural rib 56 extends a length of the internal compartment 54 of the longitudinal encasement 52, from a first end 58 to a second end 60. The structural rib 56 is attached to a surface 62 of the internal compartment 54 providing structural integrity to the support belt 50, thereby enabling creating a significant weight bearing capacity.

Both the first and second ends 58, 60 of the longitudinal encasement 52 include interconnection portions 64 that are generally triangularly shaped. The interconnection portion 64 includes a structural webbing 66 that initiates on a first side 68 of the support belt 50 and folds over to terminate on an opposite, or second side 70, of the support belt 50. The structural webbing 66 generally follows a perimeter of the interconnection portions 64. A ring 72 is included at the ends of each interconnection portion 64 of the support belt 50. The ring 72 is generally affixed to the interconnection portion 64 through a loop enclosure 74 created by the structural webbing 66. The structural rib and structural webbing are made of a flexible, durable, and strong material, preferably Dacron. The ring 72 attached to the interconnection portion 64 can be a "D" ring as shown in FIG. 6, alternatively, an "O" ring, as shown in FIG. 7.

In the second embodiment of the present invention, the first side 68 of the support belt 50 of the longitudinal encasement 52 includes a first portion 76 and a second portion 78 that creates an opening 80 for providing access to the internal compartment 54. An enclosure mechanism 82 is disposed along both perimeter edges of one side of the first and second portions 76, 78 of the longitudinal encasement 52. The enclosure mechanism 82 can be any of those known by one skilled in the art, including a zipper, snaps, hook and loop fastener, or buttons. In the present embodiment shown in FIG. 9, the enclosure mechanism is a zipper 82. The zipper 82 holds the first and second portions 76, 78 together, closing the internal compartment 54 of the longitudinal encasement 52.

Figure 11:
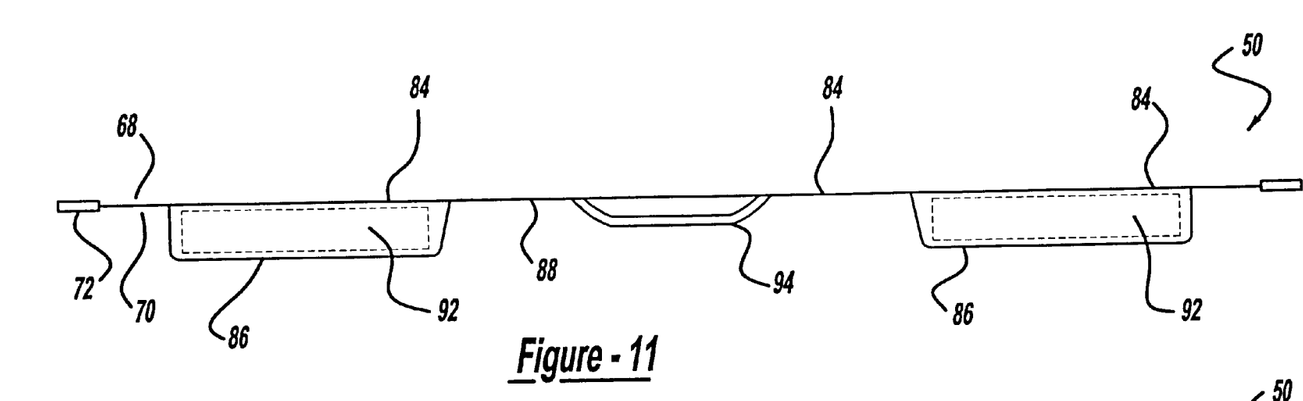
FIG. 11 is a cross sectional view along line 11–11' in FIG. 9 of the second embodiment of a support belt showing an internal compartment with support pads contained in dual lateral chambers.

In the second embodiment, the internal compartment 54 of the support belt 50 is divided into three chambers 84, whereby two lateral chambers 86 flank a central chamber 88. The chambers 84 are shown as contiguous, but divided by stitching 90 interspersed between each chamber 84. The chambers 84 can be accessed via the access opening 80 in the internal compartment 54. Support pads 92 can be selectively placed in each of the three chambers 84. As shown in FIG. 11, support pads 92 are placed in each of the lateral compartments 86. Further, a support pad 92 can be selectively placed in the central chamber 88. The use of support pads 92 in the chambers 84 is discretionary, based upon the patient's individual medical concerns and necessities.

The support pads 92 can be enclosed within launderable cases, or placed directly into the internal compartment 54. The support pad itself can be constructed of launderable materials. The longitudinal encasement 52 of the support belt 50 may also be constructed of launderable materials, as well. The support pad 92 can be constructed of any foam support padding known to one skilled in the art. A preferred material of construction is an open-cell rebounded urethane-ether foam with a rubber base, typically having a density of 6–7 lb/ft$^3$, available from such suppliers as the Foam Factory.

Figure 12:
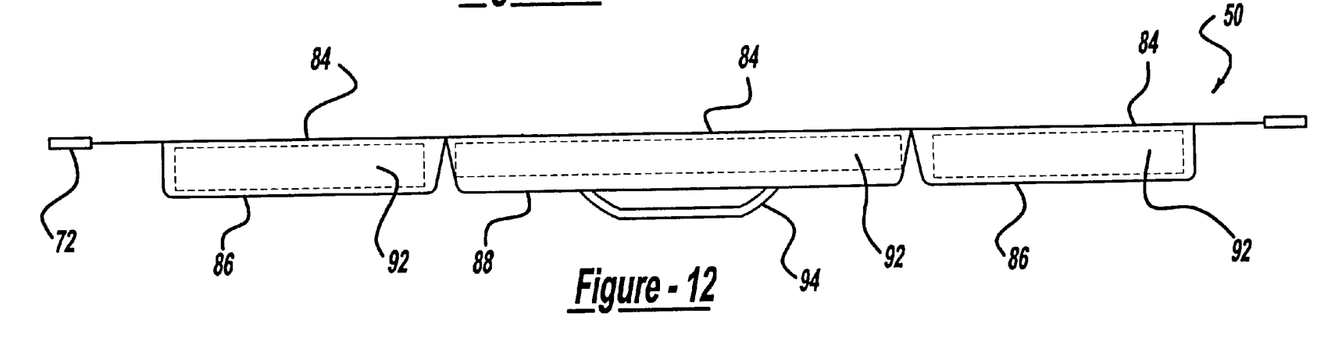
FIG. 12 is a cross sectional view along line 11–11' in FIG. 9 of the second embodiment of a support belt showing an internal compartment with support pads contained in both dual lateral chambers and a central chamber.

As the support belt 50 is placed in position surrounding a patient's back, the lateral chamber 86 support pads 92 provide cushioning to underarm and side areas. The support belt 50 cushions the patient and inhibits skin chafing and injuries. The central chamber 88 of the second embodiment may also contain a support pad 92 for cushioning contact with the patient's back, as shown in FIG. 12. The second embodiment of the present invention also contains a handle 94 disposed on the second side 70 of the support belt 50. The handle 94 is attached to a reinforcement area 96 of the second side 70 of the support belt 50. The reinforcement area 96 adds structural integrity and endurance to the longitudinal encasement 52. The handle 94 may be constructed of any number of materials, that possess strength, flexibility and durability. The handle is preferably made of Dacron.

Figures 13, 14:
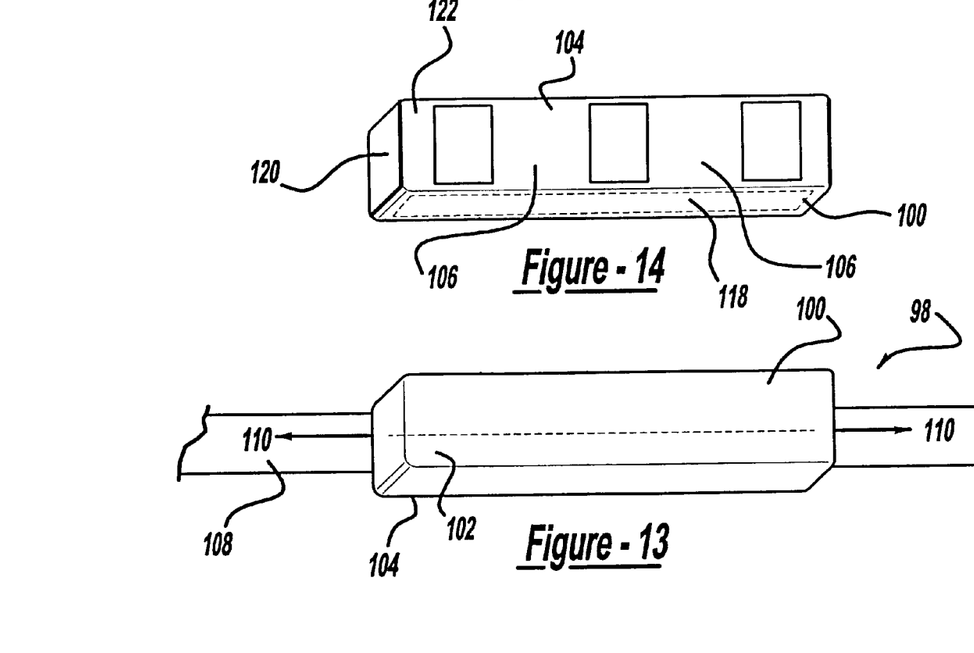
FIG. 13 shows a perspective view of a third embodiment of the present invention, a support strap showing a first side of the support strap with an attachment strap attached.
FIG. 14 shows a perspective view of the third embodiment, a support strap showing a second and opposing side of the support strap without an attachment strap attached.
Figure 15:
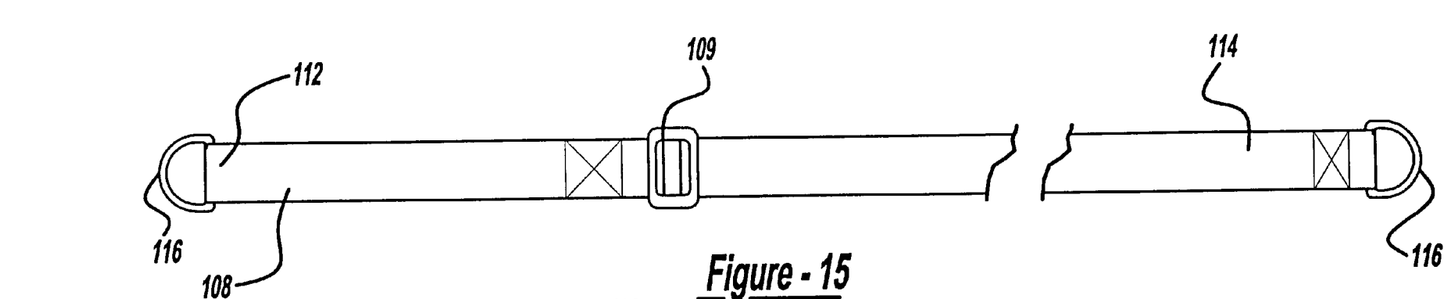
FIG. 15 shows a perspective view of the third embodiment of an adjustable length attachment strap.

A third preferred embodiment of the present invention is depicted in FIGS. 13 through 15. The third embodiment includes a support strap 98, including an encasement 100 having a first side 102 and a second, or opposing, side 104. The second side 104 includes a plurality of retainers 106 capable of receiving an attachment strap 108 threaded through each of the retainers 106. The retainers 106 attach the support strap 98 to the attachment strap 108, thereby enabling movement along the longitudinal axis 110 of the attachment strap 108. Lateral movement between the attachment strap 108 and the support strap 98, however, is substantially restricted, thereby facilitating movement of the support strap 98 without movement against the leg, inhibiting any frictional contact between the support strap 98 and delicate skin. The attachment strap 108 terminates in a first end 112 and a second end 114. A ring is 116 disposed at both the first end 112 and second end 114 of the attachment strap 108. The attachment strap 108 of the present embodiment is depicted as being an adjustable length strap, however, many variations of the attachment strap 108 are anticipated, as known by one skilled in the art. The adjustable length attachment strap may be adjusted and secured with a non-slip metal buckle 109.

The encasement 100 of the support strap 98 contains a support pad 118, and has an opening 120 at a front end 122 through which the support pad 118 can be inserted. Alternatively, the support pad can be sewn into an encasement without an opening. The support pad 118 may optionally contain a slipcover for laundering, however, the embodiment shown uses a washable foam pad. It is also anticipated that the support strap encasement 100 is optionally made of a launderable material. The support pad can be constructed of any foam support padding known to one skilled in the art. One preferred material of construction is a dry-fast, washable, open-cell, urethane-ether foam, having a density of 1–3 lb/ft$^3$, available from such suppliers as the Foam Factory.

The present invention can be used in conjunction with a patient lift device of a type commonly known in the art. Many variations of such devices are available in the industry. The present invention is designed for compatibility with any one of these devices. The patient lift device is used for caregivers to alleviate the difficulties with handling and transporting non-weight bearing or incapacitated persons. Many patient lift devices include hydraulic lift systems that are operated by manual or motorized controls. These systems enable caregivers to move or lift a patient for various necessary functions, including bathing, dressing, lavatory assistance and transporting.

Figure 16:
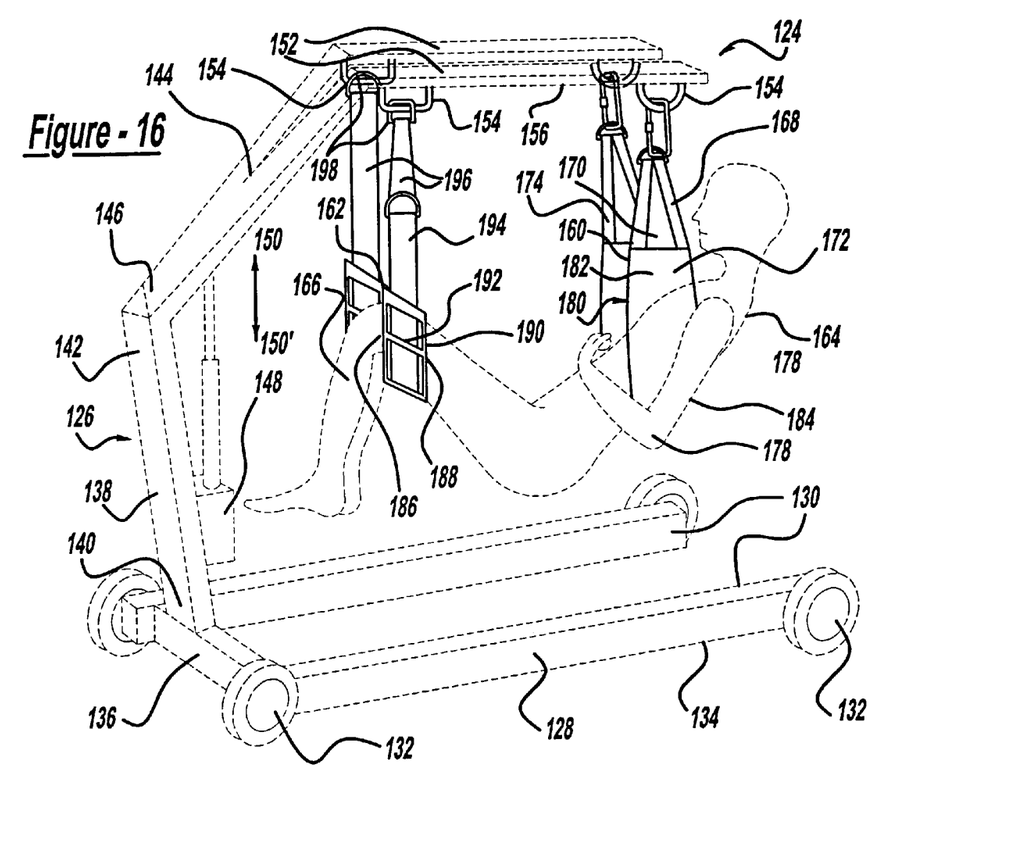
FIG. 16 shows a perspective view of a fourth embodiment of the present invention depicting a support assembly attached to a patient lift system with a suspended patient in a reclined position.
Figure 17:
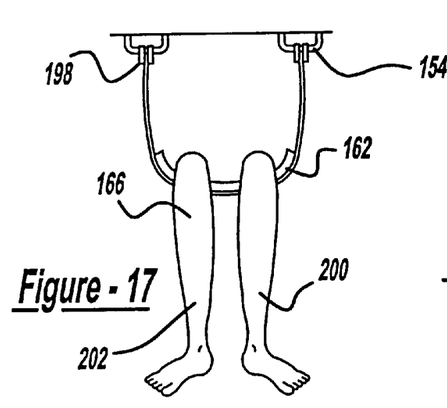
FIG. 17 shows a frontal perspective of the fourth embodiment, a support assembly with an attachment configuration of a support strap supporting a patient's legs together.
Figure 18:
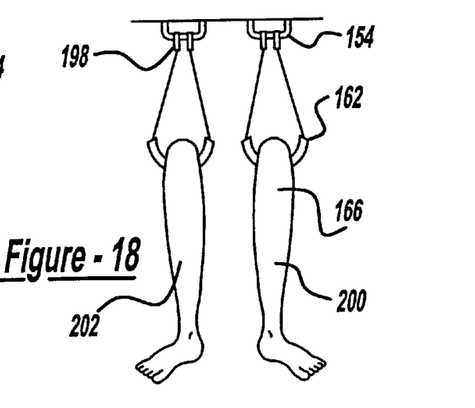
FIG. 18 shows a frontal perspective of the fourth embodiment of a support assembly with a separated attachment configuration of dual support strap supporting a patient's legs apart from one another.

With reference to FIGS. 16 through 18, a fourth preferred embodiment of the present invention is shown. A support assembly 124 is used as a three point suspension system with a patient lift device 126. The patient lift device 126 includes a base 128 with separated bars 130 to provide stability when a load is applied to the lift device 126. The separated bars 130 prevent the patient lift device 126 from overturning. The base 128 includes casters 132, or roller wheels, on the underside 134 of the separated bars 130 for mobility of the patient lift device 126. The base 128 also includes a horizontal bar 136 connecting the separated bars 130. A vertical bar 138 has a first end 140 and a second end 142, the first end 140 is mounted into the base 128 via the horizontal bar 136. The second end 142 of the vertical bar 138 is attached to a horizontal extension member 144 at a joint 146. The extension member 144 is attached to a hydraulic lift mechanism 148. The hydraulic lift mechanism 148 extends and retracts the extension member 144 along a vertical axis 150–150', varying the height of the extension member 144 as desired. The hydraulic lift mechanism 148 can operate either by motorized or manual control. The patient lift device 126 shown in FIG. 16 is a motorized hydraulic lift 148.

The extension member 144 can be a unitary body. Other variations of the patient lift device not shown here can include a support arm attached to the extension member. The extension member 144 is a unitary body in FIG. 16. The unitary extension member 144 forks into two support bars 152. The support bars 152 have litates 154, or hangers, attached to the surface directed towards the base. The litates 154 are capable of receiving attachments to suspend a patient from the patient lift device 126.

The support assembly 124 includes a support belt 160 and a support strap 162. The support belt 160, as that described in the first and second embodiment of the present invention, supports the patient's back 164, and the support straps 162, such as those described in the third embodiment of the present invention, support the patient's legs 166.

The support belt 160 can be attached to the patient lift device by the rings 168 disposed at the end of each interconnection portion 170 of the support belt 160 first and second ends 172, 174. The rings 168 can be attached directly to the connection points or litates 154 of the patient lift device 126. If an increase in the length of the support belt ring connection is needed, auxiliary clasps 176 are available for attaching to the terminal rings 168. These clasps 176 can be one of numerous designs available to one skilled in the art. The clasps shown in FIG. 16 are carabiner-style clasps for enabling quick release.

The support belt 160 wraps around the patient's torso beneath the arms 178. The first side 180 of the support belt 160 faces towards the patient's back, while the second side 182 of the support belt 160 opposes the patient's back 164. The handle 184 protrudes from the second side 182, whereby the caregiver accesses the handle 184. The handle 184 can be employed to guide movement of the suspended patient's torso 184. After the rings 168 and clasps 176 of the first and second ends 172, 174 of the support belt 160 are attached to the patient lift device 126, the torso portion 184 of the patient is suspended by the support belt. The patient position shown in FIG. 16 is reclined for situations such as where the patient is bathing or being transported to a bed. Other suspension configurations are contemplated depending on the patient's needs.

A plurality of support straps 162 such as that described in the third embodiment of the present invention are used concurrently with the support belt 160 to suspend the legs 166 of the patient. The support strap 162 wraps around the underside of the patient's thigh preferably anterior to the knee 186. The first side 188 of the support strap 162 faces the patient's leg 166, while the second side 190 of the support strap 162 opposes the patient's leg 166. The second side 190 contains retainers 192 that receive an attachment strap 194. The first and the second ends 196 of the attachment strap 194 have terminal rings 198 for attachment to the patient lift device 126 connection litates 154. The attachment strap 194 shown in FIGS. 16 through 18 is one of an adjustable length type, whereby the appropriate suspended leg height can be determined prior to connection to the patient lift device 126.

The rings 198 of the first and second ends 196 of the attachment strap 194 can be attached to the patient lift device 126 in multiple configurations. A first attachment configuration is shown in FIG. 17. The first attached configuration is desirable when it is necessary to keep the legs 166 of the patient adjacent to one another, such as during transport of the patient 158. The support strap 162 is placed beneath both legs 166. The strap rings 198 for the support strap 162 supporting the patient's legs 166 will be attached to the patient lift device/connection litates 154 directly above the left leg 200 and right leg 202 respectively. This results in a pattern of suspension that holds the legs together while the patient's body is suspended.

A second attachment configuration, as shown in FIG. 18, is a separated pattern. The separated pattern is desirable when the patient's legs 166 must be separated for various reasons. The strap rings 198 of the attachment strap 194 of the support strap 162 supporting the patient's left leg 200 will be attached to the patient lift device connection litate 154 directly above the left leg 200. The strap rings 198 of the attachment strap 194 of the support strap 162 supporting the patient's right leg 202 will be attached to the patient lift device connection litate directly above the right leg 202. This results in the legs 166 being in a separated suspended position. The separated pattern can be useful for performing various functions, including bathing, dressing, or lavatory assistance.

Figure 19:
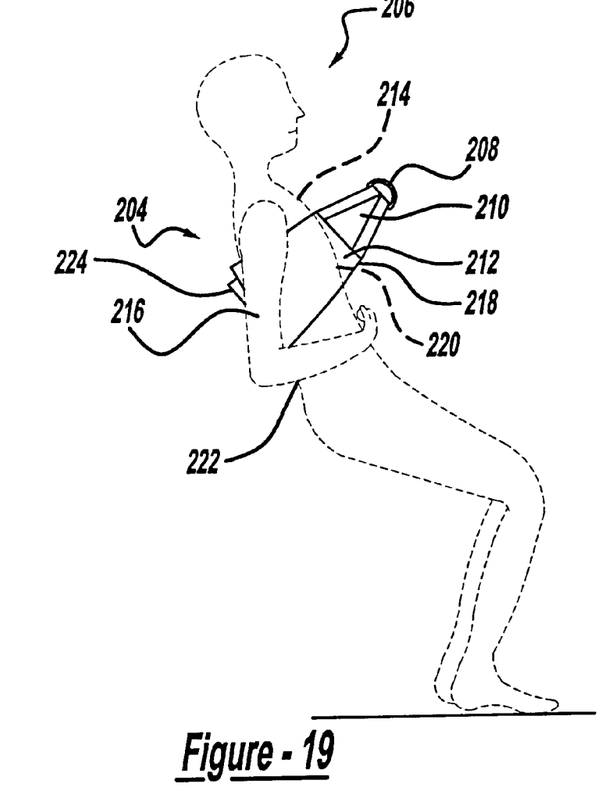
FIG. 19 shows a perspective view of a fifth embodiment of the present invention, a support belt supporting a semi-weight bearing patient.

A fifth preferred embodiment of the present invention is depicted in FIG. 19, and includes a support belt 204 similar to the support belt of the first and second embodiments. The support belt 204 is used to assist a semi-weight bearing patient 206 by partial suspension with the patient lift device, similar to suspension of the patient with the support belt in the fourth embodiment. The support belt 204 is attached to the patient lift device by the rings 208 disposed at the end of each interconnection portion 210 of the first and second ends 212 of the support belt 204. The rings 208 can be attached directly to the patient lift device connection litates. Similar to the fourth embodiment of the present invention, the option for lengthening the connection is provided using auxiliary clasps.

The support belt wraps around the patient's torso 214 beneath the arms 216. The first side 218 of the support belt 204 faces towards the patient's back 222, while the second side 220 opposes the patient's back 222. The handle 224 protrudes from the second side 220, for caregiver access to the handle 224. The handle 224 can be employed to guide movement of the suspended patient's torso 214. After the rings 208 are attached to the patient lift system, the patient 206 will has partial suspension throughout the torso area 214.

Figure 20:
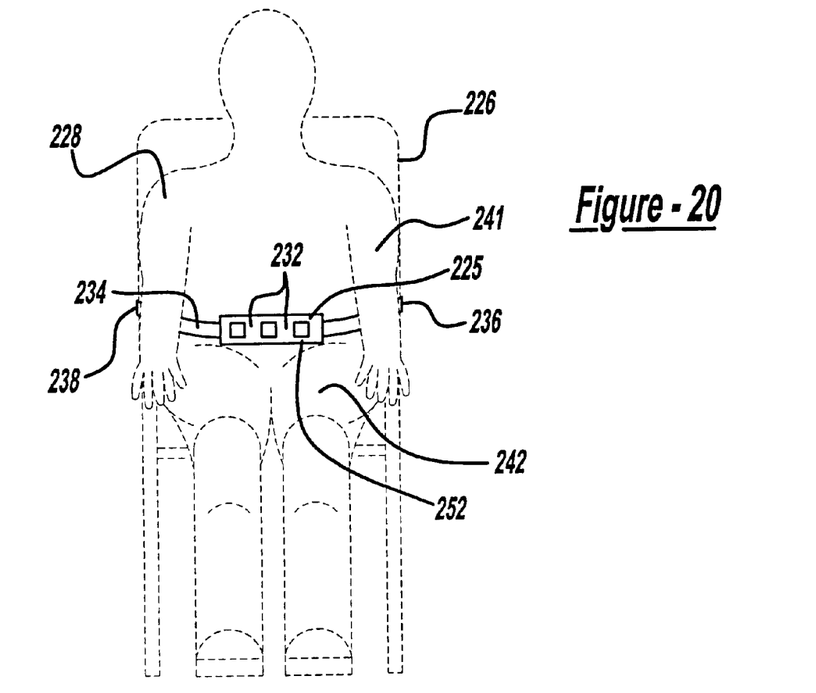
FIG. 20 shows a sixth embodiment of the present invention of a support strap used with a wheelchair patient.
Figure 21:
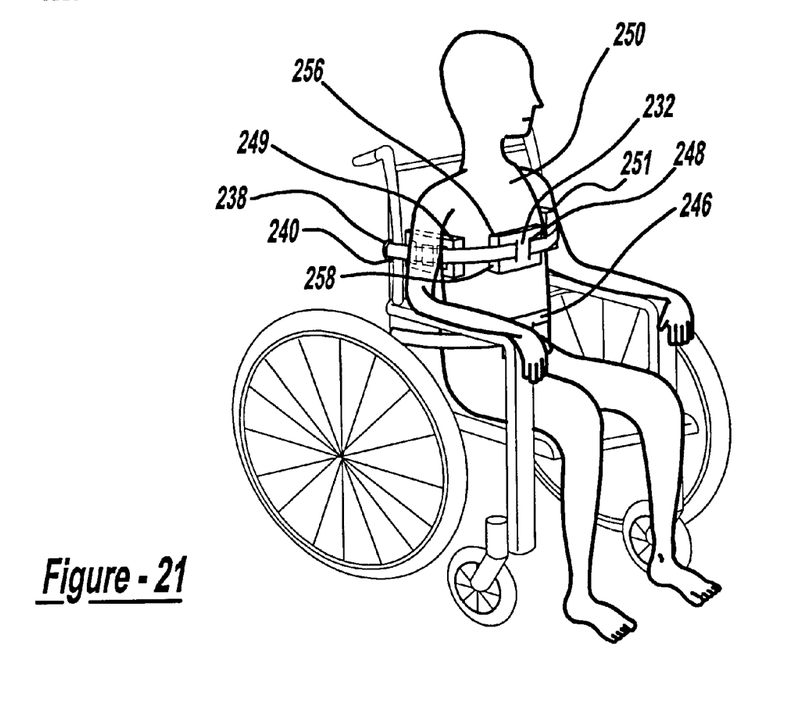
FIG. 21 shows the sixth embodiment of four support straps used with a wheelchair patient.

A sixth preferred embodiment of the present invention is generally shown in FIGS. 20 and 21. A support strap 225, similar to that of the third embodiment, is used with a wheelchair 226 to support a patient 228 lacking sufficient upper body strength.

The support strap 225 of the sixth embodiment includes an encasement having first and second sides. The first side of the support strap 225 faces the patient 228 and is pressed against the body to restrict movement. The second side includes a plurality of retainers 232, whereby each retainer 232 is capable of receiving an attachment strap 234 there through. The retainers 232 attach the support strap 225 to the attachment strap 234. The attachment strap 234 includes terminal ends 236, each having a ring 238 disposed there through. The attachment strap of the sixth embodiment is preferably an adjustable length strap; however, it is anticipated that variations of the strap may be substituted therefor.

The support strap 225 can be attached to a wheelchair 226 via the strap rings 238 to various wheelchair connection points 240. A wheelchair 226 often has prefabricated areas for attachment of the rings 238. Alternatively, the wheelchair 226 can be modified to include a hook or peg 240 to which the ring 238 can be affixed. This restricts the support strap 225 to surround the patient, allowing for appropriate support of the patient 228.

In the configuration of FIG. 20, a single support strap is used for individuals who need assistance in remaining upright in the wheelchair 226. The support strap 225 can be placed across the lower abdomen 242, or lap, of the patient. FIG. 21 shows an alternative attachment configuration, whereby four support straps 225 are used to restrain a patient 228 in need of more extensive support for remaining upright in the wheelchair 226. A primary support strap 246 is placed across the lower abdomen 242, or lap of the patient, and a secondary support strap 248 is placed across the torso 250, or chest, of the patient 228 for providing additional support. Also, two additional support straps 249, 251 are placed under the patient's arms 241 to provide cushioned support.

The encasement 252 of the support strap 225 contains a support pad 254, and has an opening 256 at a front end 258 through which a support pad 254 can be inserted. Alternatively, a support pad 254 can be sewn into the encasement 252 without any openings. The support pad 254 may optionally contain a cover; however, it is preferred that the support pad is a washable open-cell, urethane-ether foam typically having a density of 1–3 lb/ft³, available from such suppliers as Foam Factory.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A support assembly for use with a patient lift system, comprising:

a support belt comprised of a longitudinal encasement having an integral compartment, said support belt having a support belt first end and a support belt second end;

a support belt interconnection portion disposed at each of said first end and said second end, whereby each said support belt interconnection portion attaches to the patient lift system;

a central flanked lateral chambers in said internal compartment;

an access opening in said longitudinal encasement, said access opening having an enclosed mechanism to selectively provide access to said internal compartment;

a support strap having retainers attached to an exterior of said support strap;

an attachment strap attached to said support strap through said retainers, said attachment strap having an attachment strap first end and an attachment strap second end; and an attachment strap interconnection portion disposed at said attachment strap first end and said attachment strap second end, whereby each said attachment strap interconnection portion can be attached to a rigid structure to secure a patient.

2. The support assembly system according to claim 1, wherein said attachment strap is adjustable in length.

3. The support assembly according to claim 2, wherein a non-slip metal buckle is disposed along said attachment strap.

4. The support assembly system according to claim 1, whereby said lateral chambers are contiguous with said central chamber.

5. The support assembly system according to claim 1, wherein said lateral chambers contain support padding.

6. The support assembly system according to claim 1, wherein said central chamber contains support padding.

7. The support assembly system according to claim 5, wherein said support padding is constructed of launderable material.

8. The support assembly system according to claim 6, wherein said support padding is constructed of launderable materials.

9. The support assembly system according to claim 1, wherein said internal compartment houses support padding.

* * * * *